(12) United States Patent
Smith

(10) Patent No.: US 11,666,487 B2
(45) Date of Patent: *Jun. 6, 2023

(54) BREATHABLE ADHESIVE BANDAGES

(71) Applicant: Lucas Hector Izard Smith, Lake Tekapo (NZ)

(72) Inventor: Lucas Hector Izard Smith, Lake Tekapo (NZ)

(*) Notice: Subject to any disclaimer, the term of this patent is extended or adjusted under 35 U.S.C. 154(b) by 0 days.

This patent is subject to a terminal disclaimer.

(21) Appl. No.: 17/880,037

(22) Filed: Aug. 3, 2022

(65) Prior Publication Data

US 2022/0370256 A1    Nov. 24, 2022

Related U.S. Application Data

(63) Continuation of application No. 17/400,051, filed on Aug. 11, 2021, now Pat. No. 11,439,540, which is a continuation of application No. PCT/NZ2020/050016, filed on Feb. 27, 2020.

(60) Provisional application No. 62/811,033, filed on Feb. 27, 2019.

(51) Int. Cl.
*A61F 13/02* (2006.01)

(52) U.S. Cl.
CPC ........ *A61F 13/0243* (2013.01); *A61F 13/025* (2013.01); *A61F 13/0206* (2013.01); *A61F 13/0289* (2013.01)

(58) Field of Classification Search
CPC ...... A61F 13/00; A61F 13/02; A61F 13/0203; A61F 13/0253; A61F 13/00008; A61F 13/00021; A61F 13/069; A61F 13/0243; A61F 13/0206; A61F 13/025; A61F 13/0289; A61F 13/0246; A61F 13/0259; A61F 13/0263; A61F 13/0266; A61F 13/0276; A61F 13/0283; A61F 2013/0296; A61F 2013/00089; A61F 2013/00238; A61F 2013/00582; A61F 2013/00655;
(Continued)

(56) References Cited

U.S. PATENT DOCUMENTS

| 2,268,777 | A |   | 1/1942  | Scholl |           |
|-----------|---|---|---------|--------|-----------|
| 2,924,331 | A | * | 2/1960  | Hoey   | A61F 13/0203 |
|           |   |   |         |        | 206/441   |
| 4,306,551 | A |   | 12/1981 | Hymes et al. | |

(Continued)

FOREIGN PATENT DOCUMENTS

| CL | 200802858 | 9/2008 |
| CN | 1374848 A | 10/2002 |

(Continued)

OTHER PUBLICATIONS

Pailthorpe et al (WOOL482/582: Wool Processing; CH 15: "Principles of Wool Fabric Finishing") (Year: 2012).*
(Continued)

*Primary Examiner* — Caitlin A Carreiro
(74) *Attorney, Agent, or Firm* — Arc IP Law, PC; Joseph J. Mayo

(57) ABSTRACT

A breathable adhesive bandage, sticking plaster or plaster includes a fabric layer, a pad and an adhesive. The adhesive may provide only partial coverage of the fabric layer, allowing breathability. The pad and/or fabric layer may be formed from wool, such as merino wool. A backing may be applied to the adhesive layer.

20 Claims, 2 Drawing Sheets

(58) Field of Classification Search
CPC .. A61F 2013/00744; A61F 2013/15934; A61F 15/008; A61M 35/00
USPC .................. 602/41–45, 52, 54, 57, 58, 900; 128/888–894; 604/304, 307; 428/35.6
See application file for complete search history.

(56) References Cited

U.S. PATENT DOCUMENTS

| | | | |
|---|---|---|---|
| 5,120,325 A * | 6/1992 | Dow, Jr. | A61L 15/46 602/41 |
| 5,244,457 A * | 9/1993 | Karami | A61F 13/025 602/54 |
| 5,939,339 A | 8/1999 | Delmore et al. | |
| 8,460,700 B2 | 6/2013 | Singhal | |
| 9,597,234 B2 | 3/2017 | Auguste et al. | |
| 11,439,540 B2 * | 9/2022 | Smith | A61F 13/0236 |
| 2003/0064190 A1 * | 4/2003 | Carte | B32B 37/1292 156/289 |
| 2003/0073362 A1 | 4/2003 | Griesbach, III et al. | |
| 2004/0002676 A1 | 1/2004 | Siegwart et al. | |
| 2007/0212520 A1 * | 9/2007 | Furumori | A61F 13/0269 428/137 |
| 2009/0280151 A1 * | 11/2009 | Restani | D06M 16/00 424/404 |
| 2012/0310186 A1 * | 12/2012 | Moghe | A61L 15/26 156/60 |
| 2013/0018336 A1 | 1/2013 | Pernot | |
| 2013/0226062 A1 | 8/2013 | Kloeppels et al. | |
| 2015/0238365 A1 | 8/2015 | Pernot et al. | |
| 2016/0030250 A1 | 2/2016 | Caneppele et al. | |

FOREIGN PATENT DOCUMENTS

| | | |
|---|---|---|
| CN | 1475278 A | 2/2004 |
| CN | 102747530 A | 10/2012 |
| CN | 104524619 A | 4/2015 |
| CN | 103596529 B | 8/2016 |
| CN | 106367959 | 2/2017 |
| EP | 1520687 B2 | 9/2010 |
| EP | 2523698 B1 | 12/2014 |
| EP | 2653140 B1 | 3/2015 |
| EP | 2696828 B1 | 5/2017 |
| NZ | 501489 B | 8/2001 |
| NZ | 512458 B | 8/2003 |
| NZ | 517608 B | 8/2003 |
| NZ | 517482 B | 12/2003 |
| NZ | 533121 B | 2/2006 |
| NZ | 541543 B | 2/2008 |
| NZ | 549226 B | 6/2010 |
| NZ | 564778 B | 3/2011 |
| NZ | 598438 B | 8/2012 |
| NZ | 581838 B | 9/2012 |
| NZ | 589348 B | 11/2012 |
| NZ | 591869 B | 10/2013 |
| NZ | 599879 B | 9/2014 |
| NZ | 735470 A | 9/2017 |
| NZ | 711516 A | 6/2020 |
| WO | 1999059646 A1 | 11/1999 |
| WO | 01/19306 A1 | 3/2001 |
| WO | 2006047969 A1 | 5/2006 |
| WO | 2015/040177 | 3/2015 |
| WO | 20150040177 A1 | 3/2015 |
| WO | 2015/084231 A1 | 6/2015 |
| WO | WO-2015084231 A1 * | 6/2015 ............. A61K 33/34 |

OTHER PUBLICATIONS

International Search Report Opinion issued in PCT/NZ2020/050016, dated Jun. 17, 2020 (6 pages).
Written Opinion issued in PCT/NZ2020/050016, dated Jun. 17, 2020 (4 pages).
First Office Action issued in CN202080016351.5 dated May 6, 2022 (English Translation thereof); 9 pages.
Search Report issued in CN202080016351.5 dated May 6, 2022 (English Translation thereof); 9 pages.
Hodgson, et al., "Studying the impact of adhesive wound dressings on skin health parameters", Report for Wool+Aid Ltd. dated Jan. 2022 (61 pages).
"Wood-Wool as a Surgical Dressing", The British Medical Journal, Jul. 12, 1884 (1 page).
Advantages of Nonwovens.PDF; "The Nonwoven Advantage"; Avintiv technical nonwovens; accessed from technicalnonwovens.com/advantages on Dec. 15, 2021 (Year: 2021).
European Search Report issued in EP20762383.6, dated Oct. 17, 2022 (10 pages).
Second Office Action dated Nov. 3, 2022 in CN202080016351.5, and English translation thereof (including translators statement).
Office Action dated Nov. 26, 2023 in application CL202102069, and English translation thereof (including translators statement).

* cited by examiner

BREATHABLE ADHESIVE BANDAGES

RELATED APPLICATIONS

This application is a Continuation of U.S. patent application Ser. No. 17/400,051, filed 11 Aug. 2021, which is a Continuation of Patent Cooperation Treaty serial no. PCT/NS2020/050016, which claims the benefit of U.S. provisional patent application No. 62/811,033 dated 27 Feb. 2019, the specification of which are hereby incorporated herein by reference.

TECHNICAL FIELD

The technical field relates to adhesive bandages or plasters.

BACKGROUND

Adhesive bandages, also known as plasters or sticking plasters, are widely used for dressing of small cuts, wounds, blisters, burns etc. Adhesive bandages are sold under many brands including Bandaid, Elastoplast etc.

Adhesive bandages are often manufactured as individual bandages, each in its own sterile package. Adhesive bandages are also available in roll form, with the user cutting individual plasters from the roll as needed.

Adhesive bandages are often made of plastic materials with an adhesive layer attached to the plastic. This structure tends to trap moisture at the skin surface, which can create an uncomfortable or irritating skin environment.

Further, art plasters are typically made from materials that are not sustainable, not environmentally friendly and are not biodegradable e.g. plastics. Also, the growing negative market perceptions about unnecessary use of plastic lead to art products being of reduced perceived value or integrity.

While attempts have been made to provide breathable adhesive bandages (e.g. some Elastoplast fabric plasters are said to be breathable), the Applicant has found that further improvements are possible.

It would be desirable to provide an improved adhesive bandage, or at least to provide the public with a useful choice.

BRIEF SUMMARY

In one embodiment, a breathable adhesive bandage may include: a fabric layer substantially formed from wool; an adhesive layer applied to the fabric layer, the adhesive layer providing only partial coverage of the fabric layer; a pad attached to the fabric layer or adhesive layer; and a removable backing covering the pad and removably attached to the adhesive layer.

The fabric layer may be a woven layer.

Alternatively, the fabric layer may be a non-woven layer.

The fabric layer may be substantially formed from merino wool.

The fabric layer may be moisture absorbent.

The fabric layer may be a brushed fabric layer. The fabric layer may be brushed only on its outer surface.

The fabric layer may be substantially formed from wool fibres with fibre thicknesses in the range 13 to 25 microns. The fabric layer may be substantially formed from wool fibres with fibre thicknesses in the range 13 to 17 microns.

The fabric layer may be substantially formed from wool fibres with fibre thicknesses in the range 12 to 16 microns.

The fabric layer may have a weight in the range 1 to 15 ounces per square yard. The fabric layer may have a weight in the range 1 to 10 ounces per square yard.

The pad may be substantially formed from wool. The pad may be substantially formed from merino wool.

The pad may be a woven fabric pad.

Alternatively, the pad may be a non-woven fabric pad.

The pad may be formed from a fabric with a weight in the range 4 to 10 ounces per square yard.

The pad may be a moisture absorbent pad.

The adhesive may be applied in a discontinuous layer. The adhesive may be applied in a pattern of stripes. The adhesive may be applied in a pattern of wavy stripes. The adhesive may be applied in a pattern of contour or fingerprint stripes.

The adhesive may be a PVA-based adhesive.

The backing may be a paper backing. The paper may be stone paper.

Alternatively, the backing may be a biodegradable plastic material.

Alternatively, the backing may be a cotton or recycled cotton backing.

An inner surface of the backing may be coated to limit adhesion between the backing and adhesive layer.

The adhesive layer may provide 20 to 95% coverage of the base layer. The adhesive layer may provide 40 to 70% coverage of the base layer.

In one embodiment, a method of manufacturing a breathable adhesive bandage may include: providing a fabric layer; applying an adhesive layer onto the fabric layer, the adhesive layer providing only partial coverage of the fabric layer; attaching a pad to the fabric layer or adhesive layer; attaching a removable backing to the adhesive layer, the removable backing covering the pad.

The method may further include sterilising the pad.

The method may further include sterilising the fabric layer.

The sterilising may be performed by irradiation.

The method may further include brushing an outer surface of the fabric layer.

BRIEF DESCRIPTION OF DRAWINGS

The adhesive bandages or plasters described herein will be described by way of example only, with reference to the accompanying drawings, in which.

DETAILED DESCRIPTION

Figure 1:
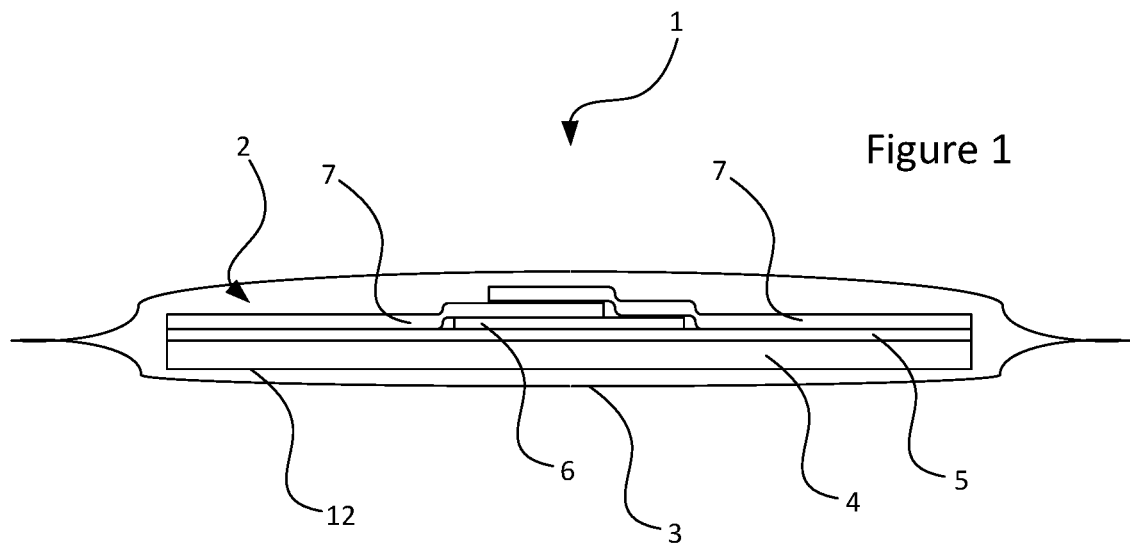
FIG. 1 is a schematic cross-section through an adhesive bandage of one embodiment.

FIG. 1 shows a breathable adhesive bandage product 1 according to one embodiment. The product 1 may include a breathable adhesive bandage 2 (also known as a sticking plaster or plaster) contained within a sealed package 3. For clarity of illustration, FIG. 1 shows the various components and layers of the product in schematic form.

The adhesive bandage 2 may include a base layer 4, an adhesive layer 5, a pad 6 and a backing 7.

In some embodiments the base layer 4 may be a fabric layer. The fabric layer may be formed substantially or entirely from wool. In some embodiments the base layer 4 may be formed substantially or entirely from merino wool. Wool has the advantages of being breathable, moisture absorbent and with natural beneficial properties. These include being naturally anti-bacterial and anti-microbial, which is beneficial in the environment of a wound. Further, wool is thought to provide some wicking and/or transport by absorption of moisture away from the skin. Wool is also biodegradable and comes from a sustainable raw material source.

The fabric layer 4 may be woven from suitable fibres. Merino wool fibres with fibre thickness around 13-25 microns, or 13 to 17 microns, or 12 to 16 microns may be suitable. The merino wool fibre thickness may be around 13, or 14, or 15, or 16, or 17, or 18, or 19, or 20, or 21, or 22, or 23, or 24, or 25 microns. The fabric layer may have a weight in the range 1 oz to 15 oz per square yard. In one embodiment the weight range may be 1 oz to 10 oz per square yard. The fabric layer may have a weight of around 1, or 2, or 3, or 4, or 5, or 6, or 7, or 8, or 9, or 10, or 11, or 12, or 13, or 14, or 15 oz per square yard. This weight was found by the applicant to provide an acceptable stretch, comfort and strength.

In other embodiments, the fabric layer may be a non-woven fabric layer, such as a felt or other non-woven fabric. A non-woven fabric layer may be formed from any suitable material including those discussed elsewhere in this specification.

In alternative embodiments the fabric layer may be formed substantially or entirely from other natural fibres such as sphagnum moss, cashmere, alpaca or yak fibres.

The pad 6 is intended to be applied topically over small cuts, wounds, blisters, burns etc (hereafter "wound"). The pad will generally be in contact with the wound. The pad 6 may be formed from any suitable material. In some embodiments, the pad 6 may be a fabric pad. The fabric pad may be formed substantially or entirely from wool. In some embodiments the pad 6 may be formed substantially or entirely from merino wool.

Wool has the advantages of being breathable, moisture absorbent and with natural beneficial properties. These include being naturally anti-bacterial and anti-microbial, which is beneficial in the environment of a wound. Further, wool may provide some wicking of moisture away from the skin. Wool is also biodegradable and sustainable.

The pad 6 may be woven from suitable fibres. Merino wool fibres with fibre thickness around 13-25 microns, or 13 to 17 microns, or 12 to 16 microns may be suitable. The pad merino wool fibre thickness may be around 13, or 14, or 15, or 16, or 17, or 18, or 19, or 20, or 21, or 22, or 23, or 24, or 25 microns.

The fabric pad may have a weight in the range 4 to 10 oz per square yard. The fabric pad may have a weight of around 1, or 2, or 3, or 4, or 5, or 6, or 7, or 8, or 9, or 10 oz per square yard.

In other embodiments the fabric pad may be a non-woven fabric pad, such as a felt or other non-woven fabric pad. A non-woven fabric pad may be formed from any suitable material including those discussed elsewhere in this specification. A non-woven merino wool felt pad may be used in some embodiments.

In alternative embodiments the pad may be formed substantially or entirely from other natural fibres such as sphagnum moss, cashmere, alpaca, yak, bamboo, cotton, sugar cane or eucalyptus fibres.

The pad and/or the base layer may be treated with any suitable agents, for example aloe vera, activated charcoal, manuka honey or cannabinoid agents. Treatment agents may promote healing. Antiseptic treatment agents may be used. Treatment agents may be used to promote absorption of moisture and/or transport of moisture. One possible treatment is the 'Woolchemy' process described in WO2016/156922.

The pad may be coated or treated to reduce the tendency of the pad to stick to the wound. The coating or treating may occur on or about at least the wound facing side of the pad and/or to the whole of the pad.

The pad 6 may be adhered to the base layer 4. The pad 6 may be adhered to the base layer 4 by the adhesive layer 5, or by a separate adhesive.

The adhesive layer 5 may be formed from a polyvinyl acetate (PVA) adhesive. Alternatively, other suitable adhesives such as those previously used in adhesive bandages (e.g. acrylate adhesives, methacrylate adhesives or epoxy diacrylates adhesives) may be used. In some embodiments natural adhesives may be used.

Dry physical adhesive layers may alternatively be used. These are layers in which the structure of the layer surface, generally through the use of very small fibres, provides an adhesive effect. At the time of writing dry adhesives are believed to be available under the brand names nanoGriptech, Setex, GeckoGrip etc. Dry adhesive effects incorporated into the base layer are intended to fall within the scope of the adhesive bandages or plasters described herein.

In some embodiments the adhesive layer may provide only partial coverage of the base layer 4. For example, the adhesive layer may provide (by area) 20 to 95% coverage, or 40 to 70% coverage, of the base layer. In selected embodiments, the adhesive layer may provide (by area) around 20, or 25, or 30, or 35, or 40, or 45, or 50, or 55, or 60, or 65, or 70, or 75, or 80, or 85, or 90, or 95% coverage. In the applied product this means that the skin is allowed to breathe through those parts of the adhesive bandage in which no adhesive is situated between the skin and base layer 4. Some air may flow, but importantly moisture is able to be moved away from the skin in these regions. In general, sufficient coverage of the adhesive should be provided such that the adhesive bandage sticks well to the skin and does not tend to peel at the edges. However, too great a coverage may limit breathability.

Figure 2:
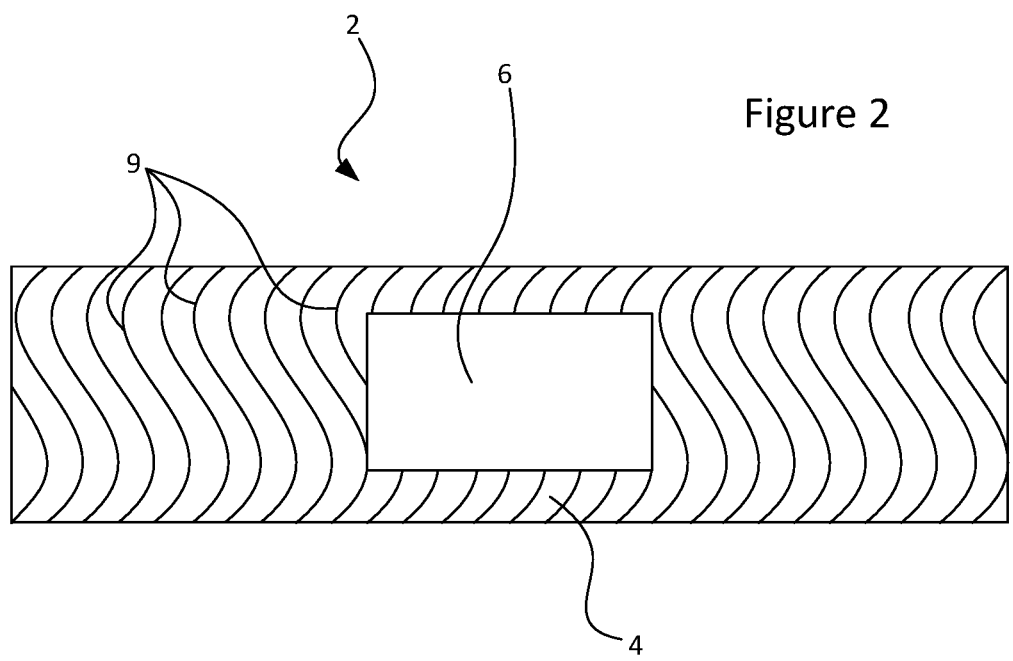
FIG. 2 is a schematic plan view of an adhesive bandage of one embodiment.
Figure 3:
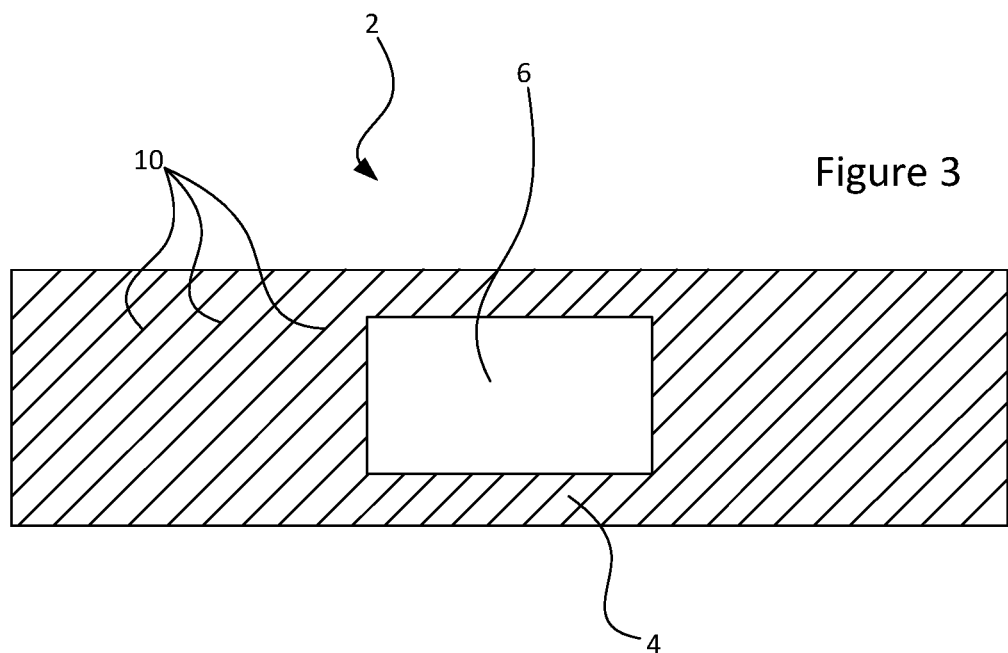
FIG. 3 is a schematic plan view of an adhesive bandage of another embodiment.
Figure 4:
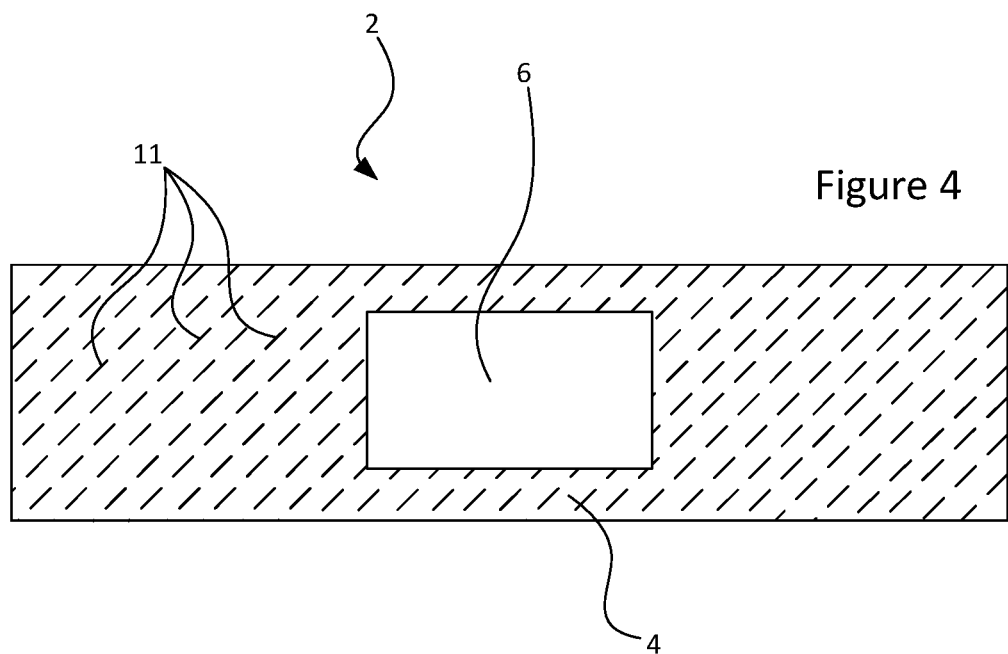
FIG. 4 is a schematic plan view of an adhesive bandage of a further embodiment.

The partial coverage of adhesive on the base layer may be achieved by applying the adhesive layer 5 in any suitable pattern of discontinuous adhesive regions. For example, FIG. 2 is a schematic plan view of an adhesive bandage 2 in which the adhesive layer 5 is applied in a series of parallel wavy stripes 9. The base layer 4 is exposed between the stripes 9. FIG. 3 shows an alternative pattern in which the adhesive layer 5 is applied in a series of parallel diagonal straight stripes 10. FIG. 4 shows an alternative pattern in which the adhesive layer 5 is applied in a series of dashed parallel diagonal straight stripes 11. In further alternatives, adhesive may be applied in a pattern of contour lines, lines forming a fingerprint pattern, other stripes or lines, dots, dashes, patches of any shape, checked patterns, hashed patterns or any other suitable pattern of discontinuous adhesive regions.

The backing 7 covers the adhesive before application of the adhesive bandage to a user's skin. The backing 7 may be formed from any suitable material. The backing may be formed from a biodegradable material. The backing may be formed from paper, such as stone paper. Alternatively, the backing may be formed from a biodegradable or compostable plastic, cotton, recycled cotton or other suitable material. The backing may be waxed or otherwise coated to prevent excessive sticking of the backing to the adhesive. The backing may be formed in two pieces, as shown in FIG. 1, or in one piece, in two pieces of different sizes, or in any other suitable configuration.

The sealed package 3 may be formed from any suitable material. The sealed package may be formed from a biodegradable material. The sealed package may be formed from paper, including stone paper. Alternatively, the sealed package may be formed from a biodegradable or compostable plastic, cotton, recycled cotton or other suitable material.

In other embodiments, no sealed package may be included. The adhesive bandages may be sold without sealed packages. Adhesive bandage may also be sold in roll form, with the user cutting a strip from the end of the roll when needed. All of these alternatives are intended to fall within the scope of the adhesive bandages or plasters described herein.

For some applications it may be desirable to modify the outer surface 12 (see FIG. 1) of the base layer. The outer surface 12 may be brushed or otherwise distressed after weaving, or after formation of a non-woven fabric. This brushed outer surface provides some extra thickness and padding or cushioning. The brushed surface is expected to be beneficial in adhesive bandages used on the feet, for example in covering blisters etc. The brushed outer surface is also believed to bind somewhat to the inside of a sock worn over the bandage, reducing rubbing and potential blister formation.

In some embodiments the adhesive bandage may be substantially or entirely formed from biodegradable materials.

The adhesive bandage may be manufactured by providing a base layer, applying an adhesive layer in any suitable pattern, attaching a pad and applying a backing. The adhesive bandage or any layers or components of the adhesive bandage (including the pad and/or base layer), may be sterilised, for example by irradiation. Optionally, for example in the case of adhesive bandages to be applied to the foot, the outer surface of the base layer may be brushed at any suitable stage of the manufacturing process. In one embodiment the base layer fabric may be brushed before application of adhesive. Adhesive bandages may be formed individually, or many bandages may be formed together before cutting into separate bandages. Optionally the adhesive bandage may be packaged in a sealed package. The components of the adhesive bandage may be as described above.

While the adhesive bandage has been shown as generally rectangular in shape, any suitable shape may be made. Adhesive bandages may be rectangular, square, round, elliptical, polygonal, or any other suitable shape.

While the adhesive bandages or plasters described herein have been illustrated by the description of the embodiments thereof, and while the embodiments have been described in detail, it is not the intention of the Applicant to restrict or in any way limit the scope of the appended claims to such detail. Further, the above embodiments may be implemented individually, or may be combined where compatible. Additional advantages and modifications, including combinations of the above embodiments, will readily appear to those skilled in the art. Therefore, the adhesive bandages or plasters described herein in their broader aspects are not limited to the specific details, representative apparatus and methods, and illustrative examples shown and described. Accordingly, departures may be made from such details without departure from the spirit or scope of the Applicant's general inventive concept.

What is claimed is:

1. A breathable adhesive bandage, comprising:
    a fabric layer comprising wool with wool fibers,
        wherein the wool fibers comprise
            a fiber thickness in a range of 13 to 25 microns;
        wherein the fabric layer comprises
            a weight in a range of 1 to 15 ounces per square yard and includes a first surface oppositely disposed from a second surface, wherein the first surface is a brushed outer surface that is formed by brushing or distressing the first surface after formation of the fabric layer to provide extra thickness and padding or cushioning to the fabric layer;
    an adhesive layer applied to the second surface of the fabric layer in a discontinuous pattern such that
        the adhesive layer is configured to cover 40% to 70% of the second surface of the fabric layer.

2. The breathable adhesive bandage as claimed in claim 1, further comprising a pad attached to the second surface of the fabric layer or to the adhesive layer.

3. The breathable adhesive bandage as claimed in claim 2, wherein the pad is formed from wool.

4. The breathable adhesive bandage as claimed in claim 3, wherein the pad is formed from merino wool.

5. The breathable adhesive bandage as claimed in claim 2, wherein the pad is a woven fabric pad.

6. The breathable adhesive bandage as claimed in claim 2, wherein the pad is a non-woven fabric pad.

7. The breathable adhesive bandage as claimed in claim 2, wherein the pad is formed from a fabric with said weight in a range of 4 to 10 ounces per square yard.

8. The breathable adhesive bandage as claimed in claim 1, further comprising a removable backing, wherein the removable backing is configured to cover a pad of the breathable adhesive bandage and removably attach to the adhesive layer.

9. The breathable adhesive bandage as claimed in claim 8, wherein the removable backing is one or more of: a paper backing, a biodegradable plastic material backing, a cotton or recycled cotton backing.

10. The breathable adhesive bandage as claimed in claim 8, wherein the removable backing comprises an inner surface, and wherein the inner surface is coated to limit adhesion between the removable backing and the adhesive layer.

11. The breathable adhesive bandage as claimed in claim 1 wherein the fabric layer is a woven layer.

12. The breathable adhesive bandage as claimed in claim 1 wherein the fabric layer is a non-woven layer.

13. The breathable adhesive bandage as claimed in claim 1, wherein the fabric layer is formed from merino wool.

14. The breathable adhesive bandage as claimed in claim 1, wherein the fabric layer is brushed or distressed only on the first surface.

15. The breathable adhesive bandage as claimed in claim 1, wherein the adhesive layer is applied in a discontinuous layer.

16. The breathable adhesive bandage as claimed in claim 1, wherein the fabric layer is formed substantially from said wool.

17. A breathable adhesive bandage, comprising:
    a fabric layer formed entirely of wool,
        wherein the fabric layer comprises
            wool fibers;
            a weight in a range of 1 to 15 ounces per square yard and includes a first surface oppositely disposed from a second surface;

wherein the first surface is a brushed outer surface that is formed by brushing or distressing the first surface after formation of the fabric layer to provide extra thickness and padding or cushioning to the fabric layer; and,
an adhesive layer applied to the second surface of the fabric layer in a discontinuous pattern such that
the adhesive layer is configured to cover 40% to 70% of the second surface of the fabric layer;
a pad attached to the second surface of the fabric layer or to the adhesive layer; and
a removable backing, wherein the removable backing is configured to
cover the pad and
removably attach to the adhesive layer.

18. The breathable adhesive bandage as claimed in claim 17, wherein the wool fibers have a fiber thickness of 13 to 25 microns.

19. A breathable adhesive bandage, comprising:
a fabric layer formed entirely of wool, the fabric layer comprising wool fibers that have a fiber thickness in a range of 13 to 25 microns;
wherein the fabric layer includes a first surface oppositely disposed from a second surface;
wherein the first surface is a brushed outer surface that is formed by brushing or distressing the first surface after formation of the fabric layer to provide extra thickness and padding or cushioning to the fabric layer; and,
an adhesive layer applied to the second surface of the fabric layer in a discontinuous pattern such that
the adhesive layer is configured to cover 40% to 70% of the second surface of the fabric layer;
a pad attached to the second surface of the fabric layer or to the adhesive layer; and
a removable backing, wherein the removable backing is configured to
cover the pad and
removably attach to the adhesive layer.

20. The breathable adhesive bandage as claimed in claim 19, wherein the fabric layer has a weight range of 1 to 15 ounces per square yard.

* * * * *